United States Patent
Gan et al.

(10) Patent No.: US 6,627,337 B2
(45) Date of Patent: Sep. 30, 2003

(54) CONVERSION OF LOW RATE ENERGY INTO HIGH RATE ENERGY BY PARALLEL DISCHARGING

(75) Inventors: Hong Gan, E. Amherst, NY (US); Esther S. Takeuchi, E. Amherst, NY (US)

(73) Assignee: Wilson Greatbatch Ltd., Clarence, NY (US)

( * ) Notice: Subject to any disclaimer, the term of this patent is extended or adjusted under 35 U.S.C. 154(b) by 140 days.

(21) Appl. No.: 09/781,830

(22) Filed: Feb. 12, 2001

(65) Prior Publication Data

US 2001/0033953 A1 Oct. 25, 2001

Related U.S. Application Data

(60) Provisional application No. 60/183,010, filed on Feb. 16, 2000.

(51) Int. Cl.[7] .......................... H01M 16/00; H01M 4/48
(52) U.S. Cl. ............................ 429/9; 429/219; 429/220; 429/223; 429/224; 429/231.1; 429/231.3; 429/231.5; 429/231.7; 429/231.95; 429/217; 429/123; 29/623.1; 320/126; 320/127; 320/135
(58) Field of Search ........................ 429/9, 123, 223, 429/245, 231.7, 219, 220, 231.1, 231.3, 231.5, 224, 217, 231.95; 320/126, 127, 135; 29/623.1

(56) References Cited

U.S. PATENT DOCUMENTS

| | | | |
|---|---|---|---|
| 2,594,988 A | 4/1952 | Portail | |
| 4,042,756 A | 8/1977 | Goebel et al. | 429/94 |
| 4,134,408 A | 1/1979 | Brownlee et al. | |
| 5,100,746 A | 3/1992 | Muller et al. | 429/94 |
| 5,180,642 A | 1/1993 | Weiss et al. | 429/90 |
| 5,219,673 A | 6/1993 | Kaun | 429/32 |
| 5,614,331 A | 3/1997 | Takeuchi et al. | 429/9 |
| 5,624,767 A | 4/1997 | Muffoletto et al. | 429/7 |
| 5,633,097 A | 5/1997 | Miller | 429/94 |
| 5,639,577 A | 6/1997 | Takeuchi et al. | 429/219 |
| 5,667,916 A | 9/1997 | Ebel et al. | 429/218 |
| 5,814,075 A | 9/1998 | Kroll | |
| 5,935,724 A | 8/1999 | Spillman et al. | |
| 6,008,625 A * | 12/1999 | Gan et al. | 320/129 |
| 6,087,809 A * | 7/2000 | Gan et al. | 320/135 |
| 6,238,813 B1 * | 5/2001 | Maile et al. | 429/9 |

FOREIGN PATENT DOCUMENTS

| | | |
|---|---|---|
| GB | 1 425 107 | 2/1976 |
| WO | WO 99/05750 | 2/1999 |
| WO | WO 99/28982 | 6/1999 |

* cited by examiner

*Primary Examiner*—Laura Weiner
(74) *Attorney, Agent, or Firm*—Michael F. Scalise

(57) ABSTRACT

An electrode configuration for use in a defibrillator battery to improve the battery capacity and its utilization efficiency by using a combination SVO cell and a $CF_x$ cell discharged in parallel, is described. In other words, the anode of the SVO cell is connected to the anode of the $CF_x$ cell and the cathode of the SVO cell is connected to the cathode of the $CF_x$ cell. The SVO cell provides a relatively high discharge rate while the $CF_x$ cell results in long service life. This results in 100% of the usable capacity from both cells being utilized.

36 Claims, 5 Drawing Sheets

CONVERSION OF LOW RATE ENERGY INTO HIGH RATE ENERGY BY PARALLEL DISCHARGING

CROSS REFERENCE TO RELATED APPLICATION

The present application claims priority based on provisional application Ser. No. 60/183,010, filed Feb. 16, 2000.

BACKGROUND OF THE INVENTION

1. Field of Invention

The present invention generally relates to the conversion of chemical energy to electrical energy. More particularly, the present invention relates to a high capacity lithium electrochemical cell designed for high rate discharge applications, such as are required to power a cardiac defibrillator.

2. Prior Art

Early ventricular cardiac defibrillators used two lithium batteries, in series, as their power source. Due to the progress of new circuit designs, the electronic circuit in a defibrillator now consumes less energy than required by earlier models. This makes it possible for the present generation of defibrillators to be powered by a single lithium electrochemical cell. With a one cell design, the requirement for high current pulse capability, or power density, is even greater due to the lowered pulsing voltage. Large electrode surface area is thus needed to accomplish this requirement. In general, when a cell's electrode surface area is increased, more inert materials (current collector, separator, etc.) are incorporated into the casing. As a result, the cell volumetric capacity is decreased. One of the concerns in such a design is the longevity of the medical device, which is dependent on the cell's capacity and power efficiency.

The capacity of an electrochemical cell is not only dependent on the electrode design and packing efficiency, it is also dependent on the type of electrode active materials used. For example, for silver vanadium oxide (SVO) cells, the E-phase having the formula $AgV_2O_{5.5}$ is preferred as the cathode active material. Its theoretical volumetric capacity is determined to be 1.37 Ah/ml. By comparison, the theoretical volumetric capacity of fluorinated carbon ($CF_x$) cathode active material (x=1.1) is 2.42 Ah/ml, which is 1.77 times greater than the theoretical capacity of SVO. However, in cardiac defibrillator applications, SVO is preferred because it can deliver relatively high current pulses or high energy within a short period of time. Although the $CF_x$ active material has higher volumetric capacity, it cannot be used in such applications due to its relatively low to medium rate of discharge capability.

Attempts to use high capacity materials, such as $CF_x$, by mixing them with a high rate cathode material, such as SVO, are described in U.S. Pat. No. 5,180,642 to Weiss et al. Batteries made from such cathode composites exhibit a relatively lower rate capability in comparison to those having SVO as the sole cathode active material. The benefit of increasing the cell's theoretical capacity by using $CF_x$ as part of the cathode mix is, in part, canceled by the lowering of this material's relatively high power capability during high rate discharge applications.

Another approach to improving the longevity of cardiac defibrillators powered by cells housed in a single casing is reported in U.S. Pat. No. 5,614,331 to Takeuchi et al. This patent describes a method of using a medium rate cell to power the circuitry of the implantable defibrillator and, separately, an SVO cell as the power supply for the device under high rate applications. The cells are described as being housed within a single casing and activated by the same electrolyte. The advantage of this method is that all of the relatively high power of the SVO cell is reserved for high power pulse discharge applications while the low power requirements of monitoring the heart beat and the like are provided by a relatively high capacity active material, such as $CF_x$. However, this method requires a very careful design to balance the capacities of the high power SVO cell with the low power $CF_x$ cell to ensure that both reach end of service life at or near the same time. Such a balance, nevertheless, is very difficult to achieve due to the variable situations in device usage by patients.

SUMMARY OF THE INVENTION

The present invention provides for improved discharge performance of lithium electrochemical cells through a new design and a new method of cell discharge. The present invention also provides a new design in defibrillator batteries to improve battery capacity and utilization efficiency, and at the same time to maintain the high current pulse discharge capability throughout service life of the battery. These objectives are achieved by discharging an SVO cell connected in parallel with a $CF_x$ cell.

Accordingly, an SVO cell for providing high power capability and a $CF_x$ cell for providing high volumetric capacity are connected together in parallel. The anode of the SVO cell is connected to the anode of the $CF_x$ cell and the cathode of the SVO cell is connected to the cathode of the $CF_x$ cell. The cells are hermetically housed in a single casing activated with the same electrolyte or hermetically housed in separate cases. The present cell configuration is particularly useful in high rate discharge applications, such as required by cardiac defibrillators. In particular, the SVO cell provides high rate discharge while the $CF_x$ cell is useful to achieve long service life. Furthermore, end of service life indication during parallel discharge of this novel cell configuration is the same as that of the SVO cell. In other words, both cells reach end of life at the same time in spite of varied usage in actual defibrillator applications. Since both cells reach end of service life at the same time, no discharge energy is wasted and there is no need to balance the capacities of both cells.

At beginning of life, a typical SVO cell has an under load voltage of around 3.2V. In comparison, a typical $CF_x$ cell has an under load voltage of around 2.8V. According to the present invention, conservation of the high power energy of the SVO cell and the low power energy of the $CF_x$ cell in an implantable cardioverter defibrillator application is achieved by discharging the two cells separately until both reach the same voltage. Then, both cells are discharged in parallel.

These and other aspects of the present invention will become more apparent to those skilled in the art by reference to the following description and to the appended drawings.

DETAILED DESCRIPTION OF THE PREFERRED EMBODIMENTS

As used herein, the term "pulse" means a short burst of electrical current of a significantly greater amplitude than that of a prepulse current immediately prior to the pulse. A pulse train consists of at least two pulses of electrical current delivered in relatively short succession with or without open circuit rest between the pulses. A typical pulse discharge is about 15.0 mA/cm$^2$ to about 30.0 MA/cm$^2$.

As used herein, the definition of CF$_x$ having a relatively high energy density but a relatively low rate capability and SVO having a relatively low energy density but a relatively high rate capability means that SVO is capable of being pulse discharge at about 15.0 mA/cm$^2$ to about 30.0 mA/cm$^2$ without its voltage falling below 1.5V. On the other hand, if CF$_x$ were to be pulse discharged under these conditions, its delivered voltage would fall below 1.5V. The pulse discharge parameter is per cathode surface area.

Figure 1:
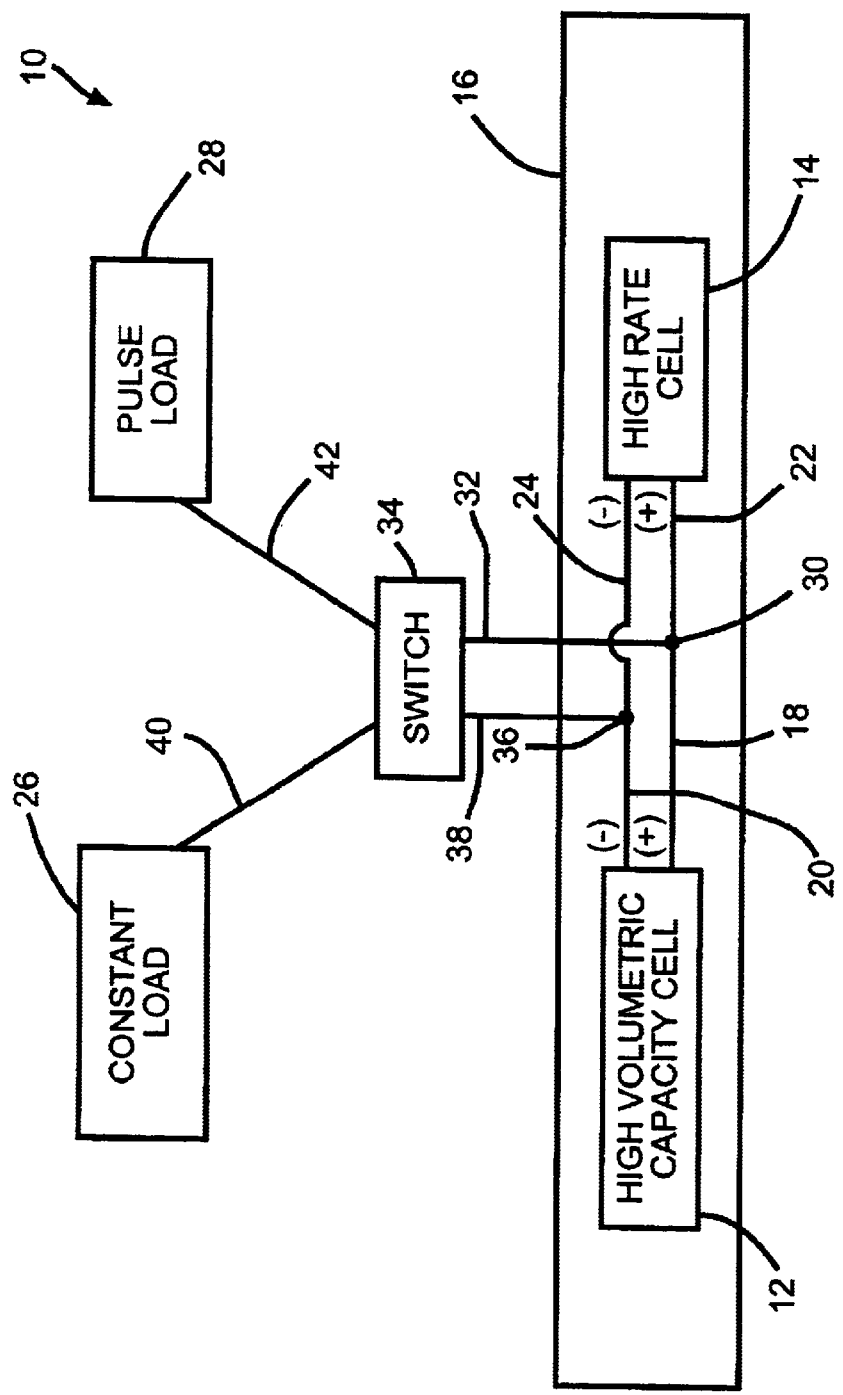
FIG. 1 is a schematic of a discharge configuration of the combination battery of the present invention.

Referring now to the drawings, FIG. 1 shows a schematic embodiment of a combination battery 10 constructed according to the present invention having both a high volumetric capacity cell 12 and a high rate cell 14 hermetically sealed in a metallic, prismatic casing 16. Both electrode assemblies are insulated from one another and activated with the same electrolyte.

As shown in FIG. 1, the high volumetric capacity cell 12 has positive and negative electrode terminals 18, 20 while the high rate cell 14 also has its own positive and negative electrode terminals 22, 24. Two different loads are applied to this battery. A constant resistance load 26 and a constant current pulse "load" 28. A device providing both a constant resistant load and a constant current pulse "load" is, for example, an implantable medical device such as a cardiac defibrillator. An implantable cardiac defibrillator is a device that requires a power source for a generally medium rate, constant resistance load component provided by circuits performing such functions as, for example, the heart sensing and pacing functions. From time to time, the cardiac defibrillator may require a generally high rate, pulse discharge load component that occurs, for example, during charging of a capacitor in the defibrillator for the purpose of delivering an electrical shock to the heart to treat tachyarrhythmias, the irregular, rapid heartbeats that can be fatal if left uncorrected. Reduction and even elimination of voltage delay during a current pulse application is important for proper device operation and extended device life.

An important aspect of the present invention is that the positive terminal 18 of the high volumetric capacity cell 12 is connected to the positive terminal 22 of the high rate cell 14 at node 30. From there, a common lead 32 connects to a switch 34. Similarly, the negative terminal 20 of the high volumetric capacity cell 12 is connected to the negative terminal 24 of the high rate cell 14 at node 36. A common lead 38 connects between node 36 and switch 34.

The switch 34 serves to direct the electrical power generated by the combination battery 10 to either the constant power load 26 via connection 40 or to the pulse load requirement via connection 42. For example, in a cardiac defibrillator, the medical device requires a relatively low level current for the maintenance of electronic monitoring circuits interrupted from time to time by high level current during device activation.

The anode electrode for both the high volumetric capacity cell 12 and for the high rate cell 14 is selected from Group IA of the Periodic Table of Elements, including lithium, sodium, potassium, etc., and their alloys and intermetallic compounds including, for example Li—Si, Li—B and Li—Si—B alloys and intermetallic compounds. The preferred anode comprises lithium, and the more preferred anode comprises a lithium alloy, the preferred lithium alloy being lithium-aluminum with the aluminum comprising from between about 0% to about 50%, by weight, of the alloy. The greater the amount of aluminum present by weight in the alloy the lower the energy density of the cell.

The anode for both the high volumetric capacity cell 12 and the high rate cell 14 is a thin metal sheet or foil of the anode metal, pressed or rolled on a metallic anode current collector, i.e., preferably comprising nickel, to form the respective anode components. As more clearly shown in FIG. 2, the respective anode components 44, 46 for both the high volumetric capacity and high rate cells 12, 14 each have an extended tab or lead 48, 50 of the same material as the anode current collector (not shown), i.e., preferably nickel, integrally formed therewith, such as by welding. The leads 48, 50 extending from the current collector of the anode components for both the high volumetric capacity cell 12 and the high rate cell 14 are contacted by a weld to the conductive metal battery casing 16 in a case-negative configuration for both cells. The battery casing 16 is preferably a prismatic housing that may comprise materials such as stainless steel, mild steel, nickel-plated mild steel, titanium or aluminum, but not limited thereto, so long as the metallic material is compatible for use with components of the cells.

Another important aspect of the present invention is that the cathode active material of the high volumetric capacity cell 12 is of any chemistry having a greater volumetric capacity than the cathode active material of the high rate cell 14. In that regard, the cathode active material of the high rate cell 14 is of any chemistry having a higher power capacity than that of the other cell 12.

Preferably, the cathode active material for the high volumetric capacity cell 12 comprises a solid active material such as fluorinated carbon represented by the formula $(CF_x)_n$ wherein x varies between about 0.1 to 1.9 and preferably between about 0.5 and 1.2 and $(C_2F)_n$ and wherein the n refers to the number of monomer units which can vary widely. These electrode active materials are composed of carbon and fluorine, and include graphitic and non-graphitic forms of carbon, such as coke, charcoal or activated carbon. Other cathode active materials include $Ag_2O$, $Ag_2O_2$, $CuF_2$, $Ag_2CrO_4$, SVO and $MnO_2$.

Before fabrication into a cathode electrode for incorporation into the cell 12, the fluorinated carbon active material is preferably mixed with a conductive additive. Suitable conductive additives include acetylene black, carbon black and/or graphite. Metals such as nickel, aluminum, titanium and stainless steel in powder form are also useful as conductive diluents when mixed with the above listed active materials. The electrode further comprises a binder material which is preferably a fluoro-resin powder such as powdered polytetrafluoroethylene (PTFE) or powdered polyvinylidene fluoride (PVDF). The preferred cathode active mixture comprises CF$_x$ combined with acetylene black and/or graphite; and PTFE. This active mixture in a dry powder form is pressed onto a conductive metal screen. Suitable materials for the cathode current collector include aluminum and titanium, preferably titanium. In some cases, the cathode electrode for the high volumetric capacity cell 12 may also be prepared by rolling, spreading or pressing a mixture of the materials mentioned above onto a suitable current collector.

The cathode electrode for the high volumetric cell 12, prepared as described above, is preferably in the form on one or more structures such as one or more cathode plates 52 operatively associated with at least one or more anode structures such as anode plate 44 of the previously described anode material. Preferably, at least one cathode plate 52 is flanked on either side by oppositely positioned anode plates 44.

The cathode electrode for the high rate cell 14 may comprise a metal element, a metal oxide, a mixed metal oxide, a metal sulfide or carbonaceous compounds, and combinations thereof. Suitable cathode active materials include silver vanadium oxide, $V_2O_5$, copper vanadium oxide, copper silver vanadium oxide (CSVO), manganese dioxide, titanium disulfide, copper oxide, copper sulfide, iron sulfide, iron disulfide, vanadium pentoxide, lithium cobalt oxide, lithium nickel oxide, lithium manganese oxide and mixtures thereof.

Preferably, the cathode active material for the high rate cell 14 comprises a mixed metal oxide formed by a chemical addition, reaction or otherwise intimate contact or by a thermal spray coating process of various metal sulfides, metal oxides or metal oxide/elemental metal combinations. The materials thereby produced contain metals and oxides of Groups IB, IIB, IIIB, IVB, VB, VIB, VIIB and VIII of the Periodic Table of Elements, which includes the noble metals and/or their oxide compounds.

By way of illustration, and in no way intended to be limiting, an exemplary cathode active material for the high rate cell 14 comprises silver vanadium oxide having the general formula $Ag_xV_2O_y$ in any one of its many phases, i.e., β-phase silver vanadium oxide having in the general formula $x=0.35$ and $y=5.18$, γ-phase silver vanadium oxide having in the general formula $x=0.80$ and $y=5.40$ and ε-phase silver vanadium oxide having in the general formula $x=1.0$ and $y=5.5$, and combination and mixtures of phase thereof.

Figure 2:
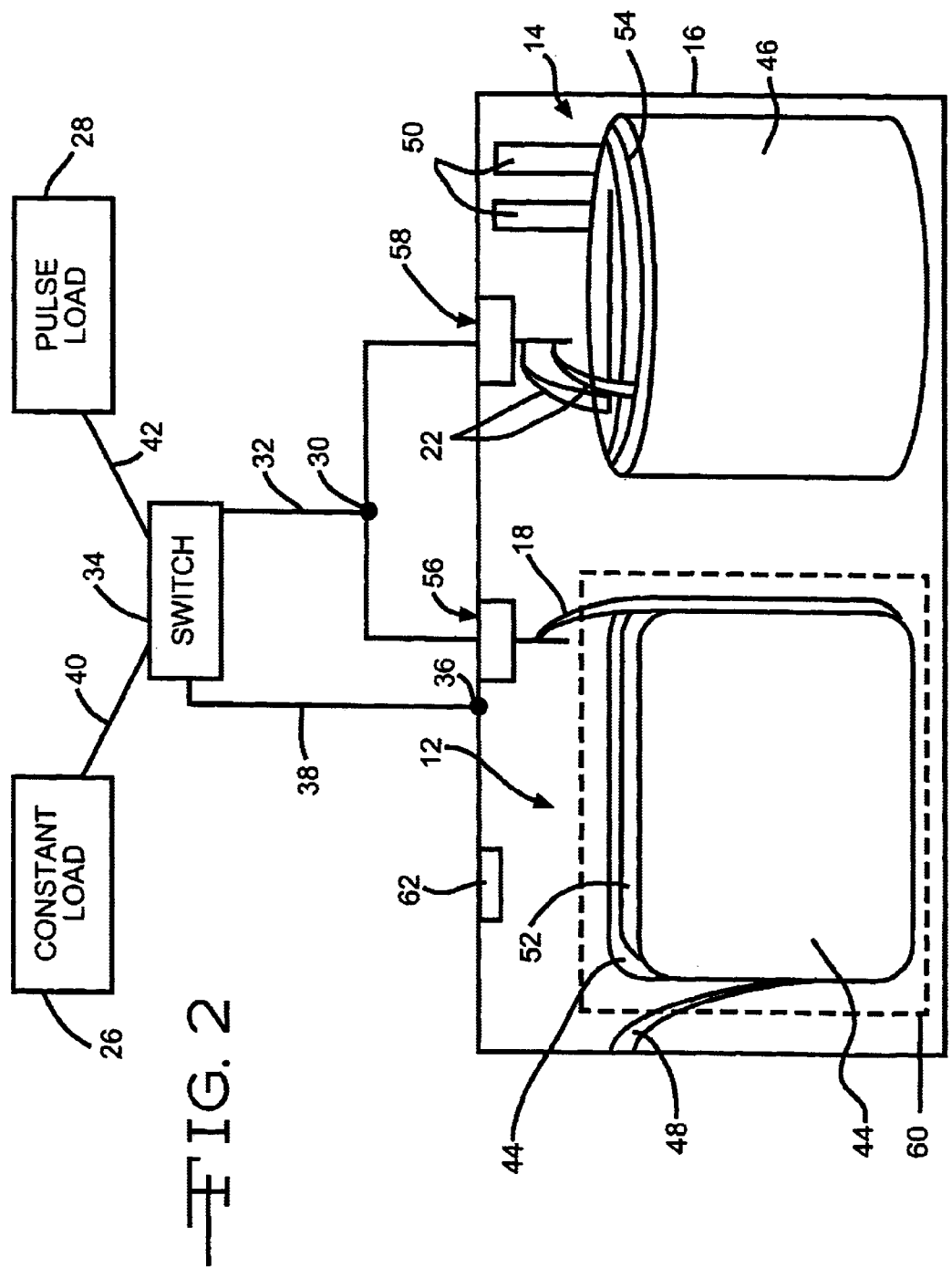
FIG. 2 is an elevational view, partly in schematic of the combination battery shown in FIG. 1.

As shown in FIG. 2, the high rate cell 14 of the combination battery 10 preferably has the cathode electrode in the form of a strip 54 wound with a corresponding strip of anode material in a structure similar to a "jellyroll". For that purpose, the cathode electrode 54 is in the form of a free-standing sheet of cathode material that has been calendered from a paste including binder and conductive additives, dried and cut to shape. The shaped cathode plate is then pressed onto at least one side and preferably both sides of a current collector screen of a suitable material such as aluminum or titanium, aluminum being preferred. A process for making cathode components useful in the high rate cell of the present combination battery is described in U.S. Pat. No. 5,435,874 to Takeuchi et al., which is assigned to the assignee of the present invention and incorporated herein by reference.

As shown in FIG. 2, the lead 18 for the cathode plates 52 of the high volumetric capacity cell 12 and the leads 22 for the cathode strip 54 of the high rate cell 14 are insulated from the casing 16 such as by respective glass-to-metal seal/terminal pin feedthroughs 56, 58. The glass used is of a corrosion resistant type having from between about 0% to about 50% by weight silicon such as CABAL 12, TA 23, FUSITE 425 or FUSITE 435. The positive terminal pin feedthroughs preferably comprise molybdenum although titanium, aluminum, nickel alloy, or stainless steel can also be used.

While the present invention is described having the anode leads 48, 50 connected to the casing 16 and the cathode leads 18, 22 insulated from the casing, the combination battery 10 can also be constructed in a case-positive configuration. This requires connecting the cathode leads 18, 22 to the casing 16 insulated from the anode terminals.

The anode components 44, 46 and the cathode structures 52, 54 for the respective high volumetric capacity and high rate cells 12, 14 are preferably sealed in their own separator envelopes (not shown for clarity) to prevent direct physical contact between the operatively associated anode electrodes and the cathode electrodes. In the case of the high volumetric capacity cell 12, an insulative bag 60 (shown in dashed lines in FIG. 2) is provided to surround the operatively associated cathode electrode and anode electrode to prevent direct contact between the high volumetric capacity and high rate cells. The insulative bag 60 is of a similar material as the separators.

The separators for both cells are of electrically insulative material to prevent an internal electrical short circuit between the electrodes, and the separator material also is chemically unreactive with the anode and cathode active materials and both chemically unreactive with and insoluble in the electrolyte. In addition, the separator material has a degree of porosity sufficient to allow flow therethrough of the electrolyte during the electrochemical reaction of the respective cells. Illustrative separator materials include fabrics woven from fluoropolymeric fibers including polyvinylidine fluoride, polyethylenetetrafluoroethylene, and polyethylenechlorotrifluoroethylene laminated with a fluoropolymeric microporous film, non-woven glass, polypropylene, polyethylene, glass fiber material, ceramics, polytetrafluoroethylene membrane commercially available under the designation ZITEX (Chemplast Inc.), polypropylene membrane, commercially available under the designation CELGARD (Celanese Plastic Company, Inc.) and a membrane commercially available under the designation DEXIGLAS (C. H. Dexter, Div., Dexter Corp.).

The combination electrochemical battery of the present invention further includes a nonaqueous, ionically conductive electrolyte which serves as a medium for migration of ions between the anode and the cathode electrodes during the electrochemical reactions of both the high volumetric capacity and the high rate cells. The electrochemical reaction at the electrodes involves conversion of ions in atomic or molecular forms which migrate from the anode to the cathode. Thus, nonaqueous electrolytes suitable for the present invention are substantially inert to the anode and cathode materials, and they exhibit those physical properties necessary for ionic transfer namely, low viscosity, low surface tension and wettability.

A suitable electrolyte for both cells has an inorganic, ionically conductive salt dissolved in a nonaqueous solvent, and more preferably, the electrolyte includes an ionizable alkali metal salt dissolved in a mixture of aprotic organic solvents comprising a low viscosity solvent and a high permittivity solvent. Preferably, the ion-forming alkali metal salt is similar to the alkali metal comprising the anode. Suitable salts include $LiPF_6$, $LiBF_4$, $LiAsF_6$, $LiSbF_6$, $LiClO_4$, $LiAlCl_4$, $LiGaCl_4$, $LiC(SO_2CF_3)_3$, $LiO_2$, $LiN(SO_2CF_3)_2$, $LiSCN$, $LiO_3SCF_2CF_3$, $LiC_6F_5SO_3$, $LiO_2CCF_3$, $LiSO3F$, $LiB(C_6H5)_4$, $LiCF_3SO_3$, and mixtures thereof. Suitable salt concentrations typically range between about 0.8 to 1.5 molar.

Low viscosity solvents include esters, linear and cyclic ethers and dialkyl carbonates such as tetrahydrofuran (THF), methyl acetate (NA), diglyme, triglyme, tetraglyme, dimethyl carbonate (DMC), 1, 2-dimethoxyethane (DME), diisopropylether, 1, 2-diethoxyethane (DEE), 1-ethoxy, 2-methoxyethane, diethyl carbonate, dipropyl carbonate, ethyl methyl carbonate, methyl propyl carbonate, ethyl propyl carbonate, and mixtures thereof, and high permittivity solvents include cyclic carbonates, cyclic esters and cyclic amides such as propylene carbonate (PC), ethylene carbonate (EC), butylene carbonate, acetonitrile, dimethyl sulfoxide, dimethyl formalize, dimethyl acetamide, γ-valerolactone, γ-butyrolacetone (GBL), N-methyl-pyrrolidone (NMP) and mixtures thereof. In the present invention, the preferred electrolyte for the high volumetric capacity cell 12 being of a $Li/CF_x$ couple is 1.0M to 1.4M $LiBF_4$ in GBL. The preferred electrolyte for the high rate cell 14 being of a Li/SVO couple is 1.0M to 1.4M $LiAsF_6$ dissolved in a 50/50 mixture (by volume) of PC and DME.

The casing header comprises a metallic lid (not shown) having a sufficient number of openings to accommodate the glass-to-metal seal/terminal pin feedthroughs 56, 58 for the cathode electrodes of the high volumetric capacity and the high rate cells. An additional opening 62 is provided for electrolyte filling. The casing header comprises elements having compatibility with the other components of the electrochemical cells and is resistant to corrosion. The battery is thereafter filled with the electrolyte solution described hereinabove and hermetically sealed such as by close-welding a stainless steel plug over the fill hole 62, but not limited thereto.

It is believed that throughout the discharge life of the cells 12, 14, all the pulse discharge energies are provided by the SVO cell. Above 2.9V, the $CF_x$ cell does not discharge. Instead, the SVO cell provides all of the discharge energies including those required for pulse discharging as well as for background monitoring. At this stage, the $CF_x$ cell is polarized to the SVO cell. Once the cells are discharged to the working voltage of the $CF_x$ cell (2.9V or below), both the SVO cell and the $CF_x$ cell provide energy for background load discharging. However, only the SVO cell provides energy for high rate pulsing discharge. After the SVO cell is pulse discharged, the potential of the SVO cell tends to drop due to loss of capacity. When the background voltage of the SVO cell drops below the working voltage of the $CF_x$ cell, the SVO cell is charged by the parallel connected $CF_x$ cell to bring both cells' background voltages to a equal value. Therefore, in practice, the SVO cell acts as a rechargeable cell and at the same time the $CF_x$ cell acted as a charger. As a result, both cells reach end of service life at the same time.

Accordingly, the high volumetric capacity cell 12 connected in parallel with the high rate cell 14 provides the battery dischargeable to deliver a relatively low electrical current on the order of about 1 microampere to about 100 milliamperes for the constant load 26 requirement. At such time as electrical energy is needed for the pulse load 28 requirement, the high rate cell 14 provides electrical current on the order of about 1 amp to about 4 amps.

It should be pointed out that the high volumetric capacity cell 12 and the high rate cell 14 of the present combination battery 10 can be housed in their own casings. In this case, they are each activated by the electrolytes described above. In another embodiment of the present invention, the cells 12, 14 reside in a single casing and are preferably activated with an electrolyte comprising $LiAsF_6$ in DME/PC.

The following examples describe the manner and process of a combination battery according to the present invention, and they set forth the best mode contemplated by the inventors of carrying out the invention, but they are not to be construed as limiting.

EXAMPLE I

Fifteen Li/SVO cells were constructed in the following manner. Lithium anode material was pressed on a nickel current collector screen and silver vanadium oxide cathode material was pressed on a titanium current collector screen. A prismatic cell stack assembly configuration with two layers of microporous membrane polypropylene separator sandwiched between the anode and cathode was prepared. The electrode assembly was then hermetically sealed in a stainless steel casing in a case negative configuration after having been activated with an electrolyte of 1.0M $LiAsF_6$ in a 1:1 volume ratio of PC and DME. The theoretical capacity Li/SVO cells built in this manner is 2345 mAh.

Nine $Li/CF_x$ cells were built in the following manner. Lithium anode material was pressed on a titanium current collector screen and $CF_x$ cathode material was pressed on a titanium current collector screen. A prismatic cell stack assembly configuration with two layers of polypropylene separator sandwiched between the anode and cathode was prepared. The electrode assembly was then hermetically sealed in a titanium casing in a case negative configuration after having been activated with an electrolyte of 1.0M $LiBF_4$ in GBL. The theoretical capacity of the $Li/CF_x$ cells built in this manner is 1315 mAh.

Figure 3:
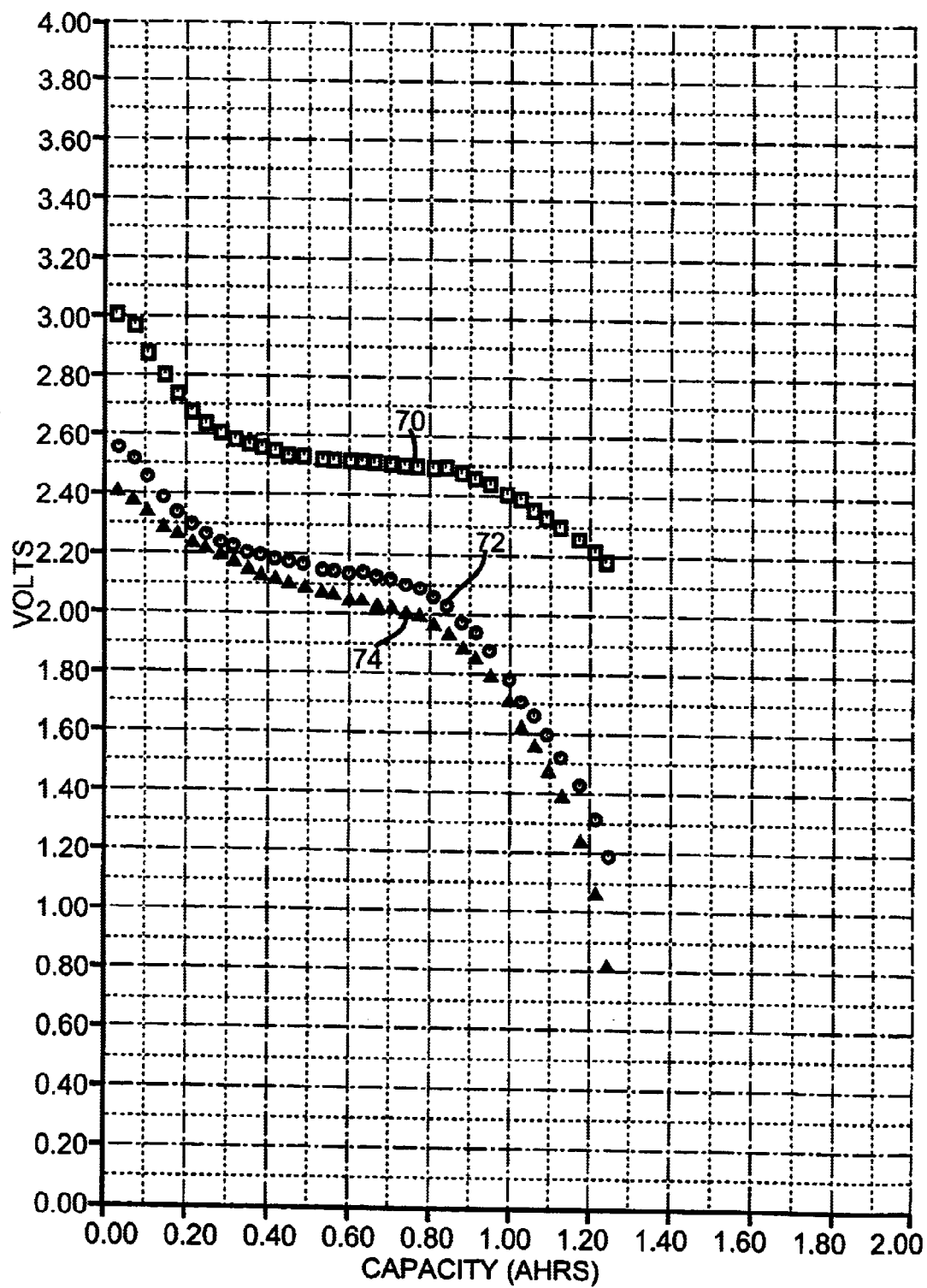
FIG. 3 is a graph constructed from the pulse discharge of a Li/SVO cell.

Before the parallel discharge test, 15 SVO cells were predischarged to remove about 644 mAh of capacity. Then, six of the cells were discharged under a 17.4 kΩ load interrupted by pulse trains applied twice a week. The pulse trains consisted of four 10 second 2.0 Amp pulses with a 15 second rest between each pulse. All six cells were discharged in this manner to end of life, and exhibited with very similar and characteristic SVO cell behavior. The average discharge capacity to various voltage cut offs are summarized in FIG. 3 and below in Table 1. In FIG. 3, curve 70 was constructed from the background voltage of a representative one of the Li/SVO cells, curve 72 is of the pulse 1 minimum (P1 min.) and curve 74 is of the pulse 4 minima (P4 min.) It should be pointed out that the total capacity values set forth in Table 1 were derived by adding the 644 mAh of predischarge capacity plus the capacity read from the p4 min. curve 74 of FIG. 3 to the various voltage cut-offs.

Figure 4:
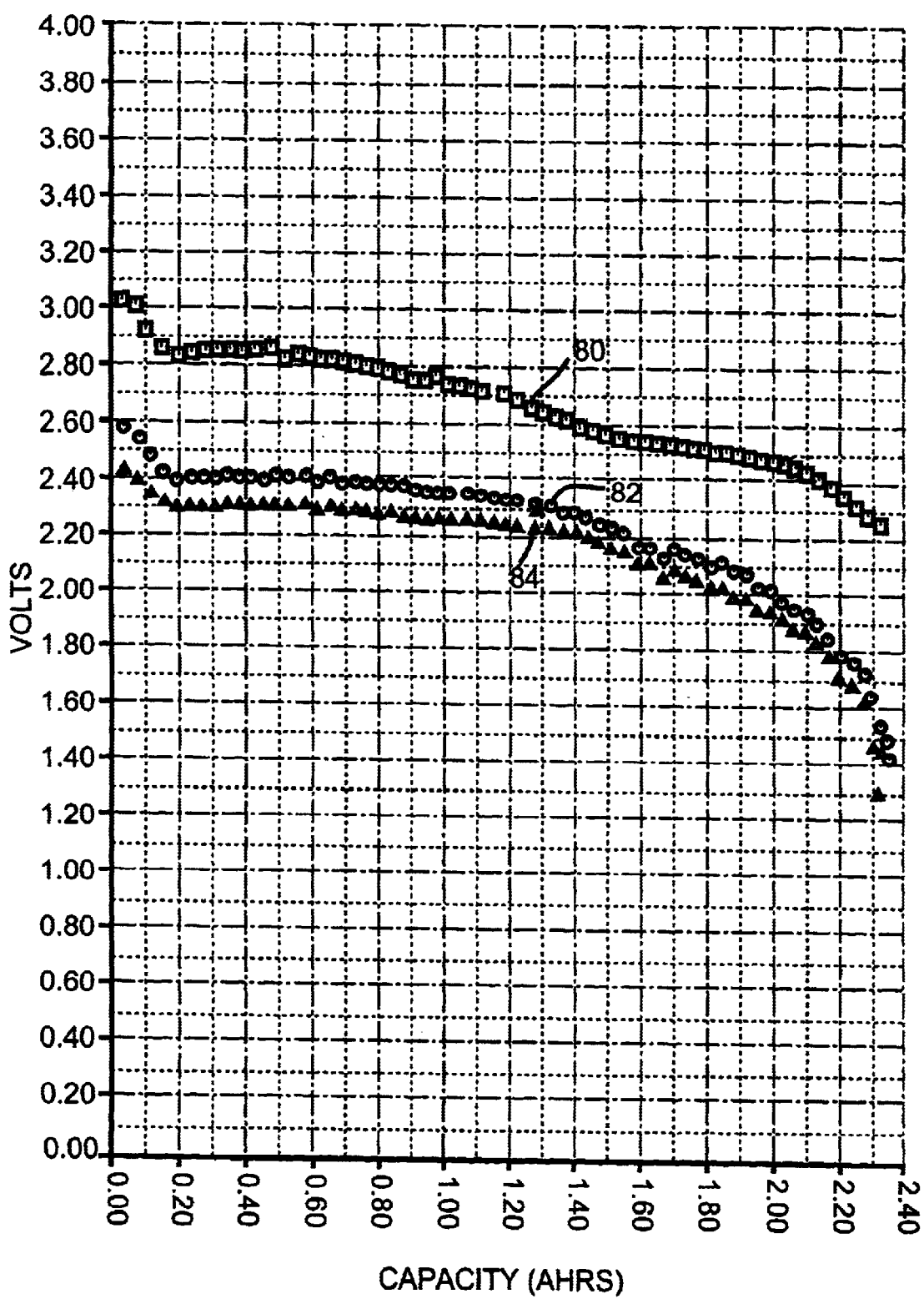
FIG. 4 is a graph constructed from the pulse discharge of a Li/SVO connected in parallel with a Li/$CF_x$ cell.

The remaining nine SVO cells were connected in parallel with the $CF_x$ cells to provide nine battery assemblies according to the present invention. As before, these battery assemblies were discharged under a 17.4 kΩ load interrupted by pulse trains applied twice a week. Similar results were observed for all nine battery assemblies. Interestingly, in addition to the 2.5V to 2.6V voltage plateau typically observed for an SVO cell, another voltage plateau at around 2.8V was observed. The average discharge results for the nine $SVO/CF_x$ cell assemblies are summarized in FIG. 4 and in Table 1. In FIG. 4, curve 80 was constructed from the background voltage of the parallel discharged Li/SVO and $Li/CF_x$ cells, curve 82 is of the P1 min. of these cells and curve 84 is of the P4 min. As with FIG. 3, the total capacity values set forth in Table 1 were derived from by adding the 644 mAh of predischarge capacity to the capacity read from the p4 min. curve 84 to the various voltage cut-offs.

TABLE 1

| | Total Capacity at Voltage Cut Off (mAh) | | | | | |
|---|---|---|---|---|---|---|
| Cell | 2.0 V | DOD | 1.7 V | DOD | 1.5 V | DOD |
| SVO | 1469 | 62.6% | 1659 | 70.7% | 1754 | 74.8% |
| SVO/CF$_x$ | 2554 | 69.8% | 2824 | 77.2% | 2894 | 79.1% |
| ΔCapacity | 1085 | | 1165 | | 1140 | |

From Table 1 and FIGS. 3 and 4, it can be seen that at each voltage cut off, the parallel discharged cell assemblies delivered higher total capacities with significantly higher total discharge efficiencies than the individual SVO cells. The cell background voltages were about 2.51V at a 2.0V cut off, about 2.41V at a 1.7V cut off and about 2.35V at a 1.5V cut off. At these background voltages, a single $CF_x$ cell typically delivers discharge capacities of about 1148 mAh (2.5 1V), about 1152 mAh (2.41V) and about 1170 mAh (2.35V), respectively under a 16.5 kΩ load. Thus, in the above example, almost 100% of the $CF_x$ deliverable capacity was converted into high power SVO energy.

EXAMPLE II

Figure 5:
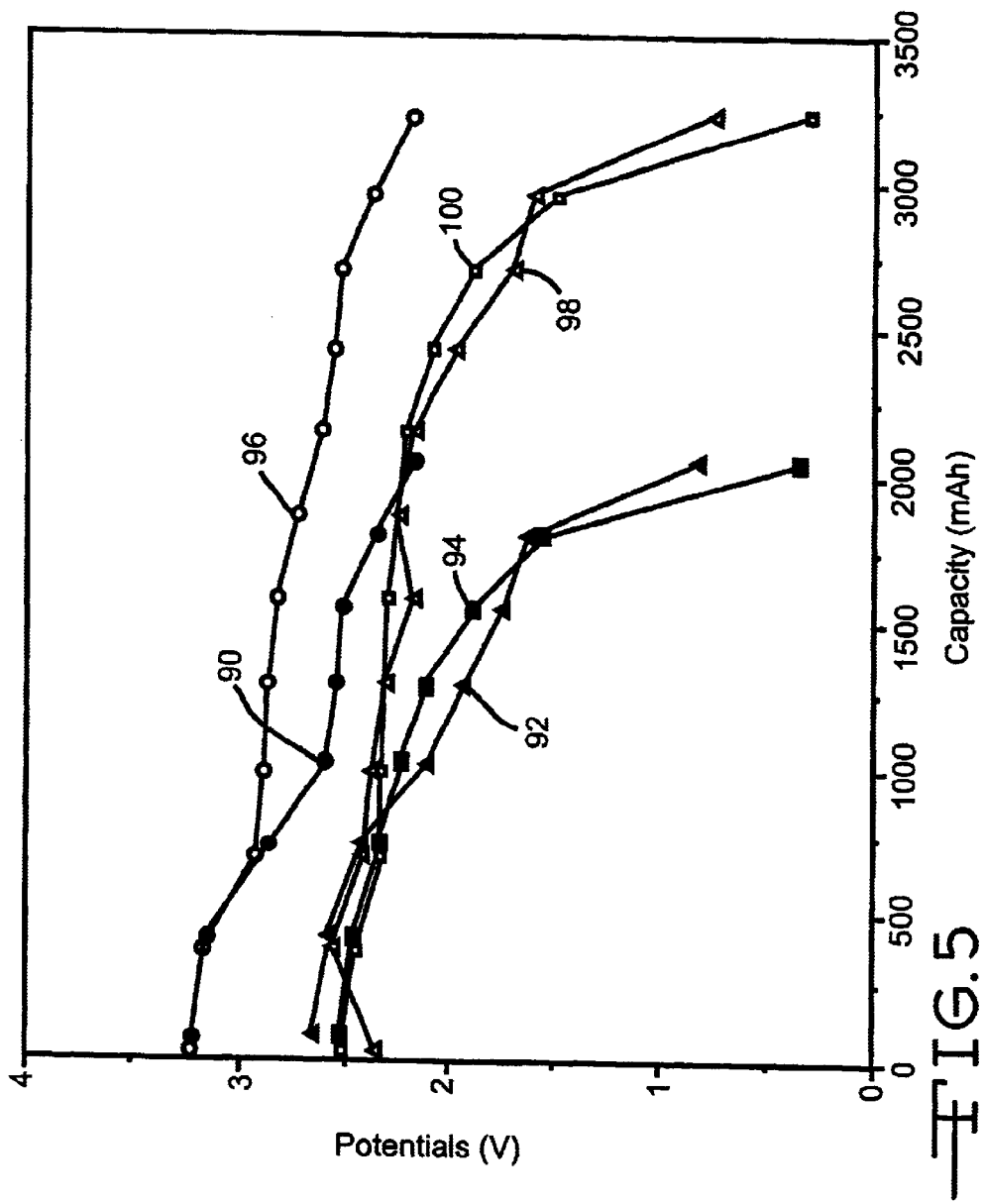
FIG. 5 is a graph constructed from the pulse discharge of a single Li/SVO cell in comparison to the pulse discharge of a Li/SVO cell connected in parallel with a Li/CF$_x$ cell.

Two SVO cells and one $CF_x$ cell were constructed in a similar manner as those described in Example I. One of the SVO cells was discharged under a 9.53 kΩ load interrupted by pulse trains applied every 39 days. The other SVO cell was parallel connected to a $CF_x$ cell according to the present invention. The resulting cell pack was then discharged under a 9.53 kΩ load interrupted every 39 days by pulse trains. In both cases, the pulse trains were similar to those described above. The results are summarized as a capacity vs. potential plot in FIG. 5. In this graph, curve 90 was constructed from the prepulse of the Li/SVO cell, curve 92 from the pulse 1 min. and curve 94 from the pulse 4 min. In contrast, curve 96 was constructed from the prepulse of the Li/SVO/$CF_x$ cell, curve 98 from the pulse 1 min. and curve 100 from the pulse 4 min. of this present invention cell.

In the initial three pulse trains, both tests presented similar cell behavior. The background voltages and pulse minimum voltages were almost identical and were typical of SVO cell behavior. After pulse train 3, however, the single SVO cell background voltage dropped to the 2.5V to 2.6V voltage plateau at pulse trains 4, 5 and 6. For the combination SVO/$CF_x$ cells, the background voltages were maintained at the 2.8V to 2.9V voltage plateau, which is the typical discharge voltage of a $CF_x$ cell. At pulse train 7, the background voltage of the single SVO cell dropped to 2.35V while the combination cells maintained their background voltage at 2.72V. In addition, the pulse minimum potentials of the parallel SVO/$CF_x$ cells was still 2.26V, which is substantially higher than that of the single SVO cell at 1.54V.

The single SVO cell reached end of life (EOL) by pulse train 8 while the parallel SVO/$CF_x$ cells did not reach EOL until pulse train 12. By comparing the cell delivered capacity at EOL for the above two tests, the capacity difference was determined to be about 1,188 mAh, which is consistent with the results obtained in Example I. This added discharge capacity is attributed to the $CF_x$ cell. These results indicated that during a long term discharge test of the SVO/$CF_x$ parallel cells, the low power $CF_x$ energy was converted to high power SVO energy. The utilization of $CF_x$ energy was also quantitative.

Conclusion

The above examples prove the feasibility of parallel discharging a high power cell, such as an SVO cell, with a high capacity cell, such as a $CF_x$. By doing so, the energy of the high volumetric capacity $CF_x$ cell is quantitatively converted into or used as the high power energy of the SVO cell.

It is appreciated that various modifications to the inventive concepts described herein may be apparent to those skilled in the art without departing from the spirit and scope of the present invention defined by the hereinafter appended claims.

What is claimed is:
1. An electrochemical battery, comprising:
 a) a casing;
 b) a first electrochemical cell housed inside the casing and comprising:
  i) a first anode comprising lithium electrically associated with a first anode current collector;
  ii) a first anode terminal connected to the first anode current collector;
  iii) a first cathode of fluorinated carbon electrically associated with a first cathode current collector;
  iv) a first cathode terminal connected to the first cathode current collector; and
 c) a second electrochemical cell housed inside the casing and comprising:
  i) a second anode comprising lithium electrically associated with a second anode current collector;
  ii) a second anode terminal connected to the second anode current collector;
  iii) a second cathode of silver vanadium oxide electrically associated with a second cathode current collector;
  iv) a second cathode terminal connected to the second cathode current collector; and
  v) an electrolyte activating the first and second electrochemical cells, wherein the casing does not have a wall separating the first cell from the second cell so that the activating electrolyte is common to both cells; and
 d) a common anode lead for the first and second anode terminals connectable to a load and a common cathode lead for the first and second cathode terminals connectable to the load.

2. The electrochemical battery of claim 1 wherein the first and second cells are dischargeable under a substantially constant discharge rate and a current pulse discharge application.

3. An electrochemical battery, comprising:
 a) a casing;
 b) a first electrochemical cell housed within the casing, the first cell comprising:
  i) a first anode comprising alkali metal electrically associated with a first anode current collector connected to a first anode terminal;
  ii) a first cathode of a first cathode active material electrically associated with a first cathode current collector connected to a first cathode terminal; and
 c) a second electrochemical cell housed within the casing, the second cell comprising:
  i) a second anode comprising alkali metal electrically associated with a second anode current collector connected to a second anode terminal;
  ii) a second cathode of a second cathode active material different than the first cathode active material and electrically associated with a second cathode current collector connected to a second cathode terminal; and
  iii) a nonaqueous electrolyte activating the first and second electrochemical cells, wherein the casing does not have a wall separating the first cell from the second cell so that the activating electrolyte is common to both cells;
 d) wherein the first cell is connected in parallel to the second cell by a common anode lead for the first and second anode terminals connectable to a load and a common cathode lead for the first and second cathode terminals connectable to the load; and e) wherein the first cathode active material has a relatively high energy density but a relatively low rate capability and the second cathode active material has a relatively low energy density but a relatively high rate capability.

4. The electrochemical battery of claim 3 wherein the first and second cells are dischargeable under a substantially constant discharge rate and under a current pulse discharge application.

5. The electrochemical battery of claim 3 wherein the first and second anode current collectors are electrically connected to the casing as the common anode lead.

6. The electrochemical battery of claim 3 wherein the first and second cathode terminals are electrically insulated from the casing.

7. The electrochemical battery of claim 3 wherein the first and second anode terminals are electrically insulated from the casing.

8. The electrochemical battery of claim 3 wherein the anode is comprised of lithium.

9. The electrochemical battery of claim 3 wherein the anode comprises a lithium-aluminum alloy.

10. The electrochemical battery of claim 9 wherein the aluminum comprises from between about 0% to about 50% by weight of the anode alloy.

11. The electrochemical battery of claim 3 wherein the nonaqueous electrolyte comprises a first solvent selected from the group consisting of an ester, an ether, a dialkyl carbonate, and mixtures thereof, and a second solvent selected from the group consisting of a cyclic carbonate, a cyclic ester, a cyclic amide, and mixtures thereof.

12. The electrochemical battery of claim 11 wherein the first solvent is selected from the group consisting of tetrahydrofuran, methyl acetate, diglyme, triglyme, tetraglyme, 1,2-dimethoxyethane, diisopropylether, 1,2-diethoxyethane, 1-ethoxy,2-methoxyethane, dimethyl carbonate, diethyl carbonate, dipropyl carbonate, ethyl methyl carbonate, methyl propyl carbonate, ethyl propyl carbonate, and mixtures thereof.

13. The electrochemical battery of claim 11 wherein the second solvent is selected from the group consisting of propylene carbonate, ethylene carbonate, butylene carbonate, acetonitrile, dimethyl sulfoxide, dimethyl formamide, dimethyl acetamide, γ-valerolactone, γ-butyrolactone, N-methyl-pyrrolidone, and mixtures thereof.

14. The electrochemical battery of claim 3 including providing an alkali metal salt in the electrolyte, the alkali metal salt being selected from the group consisting of $LiPF_6$, $LiBF_4$, $LiAsF_6$, $LiSbF_6$, $LiClO_4$, $LiAlCl_4$, $LiGaCl_4$, $LiC(SO_2CF_3)_3$, $LiO_2$, $LiN(SO_2CF_3)_2$, $LiSCN$, $LiO_3SCF_2CF_3$, $LiC_6F_5SO_3$, $LiO_2CCF_3$, $LiSO_3F$, $LiB(C_6H_5)_4$, $LiF_3SO_3$, and mixtures thereof.

15. The electrochemical battery of claim 3 wherein the first cathode active material is selected from the group consisting of $CF_x$, $Ag_2O$, $Ag_2O_2$, $CuF$, $Ag_2CrO_4$, $MnO_2$, silver vanadium oxide, and mixtures thereof.

16. The electrochemical battery of claim 3 wherein the second cathode active material is selected from the group consisting of silver vanadium oxide, copper silver vanadium oxide, $V_2O_5$, $MnO_2$, $LiCoO_2$, $LiNiO_2$, $LiMnO_2$, $CuO_2$, $TiS$, $Cu_2S$, $FeS$, $FeS_2$, copper oxide, copper vanadium oxide, and mixtures thereof.

17. The electrochemical battery of claim 3 wherein both the first and second cathodes comprise from between about 80 weight percent to about 99 weight percent of the respective first and second cathode active materials.

18. The electrochemical battery of claim 3 wherein at least one of the first and second cathodes further comprises a binder material and conductive additives.

19. The electrochemical battery of claim 18 wherein the binder material is a fluoro-resin powder.

20. The electrochemical battery of claim 18 wherein the conductive additives are selected from the group consisting of carbon, graphite powder, acetylene black, and mixtures thereof.

21. The electrochemical battery of claim 3 wherein the first and second cathodes comprise about 0 to 3 weight percent carbon, about 1 to 5 weight percent of a powder fluoro-resin and about 94 to 99 weight percent of the respective first and second cathode active materials.

22. The electrochemical battery of claim 3 wherein the cathode of at least one of the first and second cells is formed of a cathode sheet associated with the anode in a jellyroll configuration.

23. In combination with an implantable medical device requiring electrical power for a monitoring function and a device operating function, a battery comprising:
a) a first cell having a first anode comprising lithium connected to a first anode terminal and a first cathode comprising fluorinated carbon connected to a first cathode terminal;
b) a second cell having a second anode comprising lithium connected to a second anode terminal and a second cathode comprising silver vanadium oxide connected to a second cathode terminal; and
c) a casing containing the first and second cells connected in parallel and activated by a nonaqueous electrolyte, wherein the casing does not have a wall separating the first cell from the second cell so that the activating electrolyte is common to both cells.

24. An electrochemical battery, which comprises:
a) a first cell having a first anode and a first cathode of a first cathode active material of a relatively high energy density but a relatively low rate capability;
c) a second cell having a second anode and a second cathode of a second cathode active material of a relatively low energy density but a relatively high rate capability;
c) a casing housing the first cell and the second cell activated by an electrolyte, wherein the casing does not have a wall separating the first cell from the second cell so that the activating electrolyte is common to both cells; and
d) wherein the first cell is connected in parallel to the second cell so that first and second cells are dischargeable together at a relatively low electrical current of about 1 microampere to about 100 milliamperes and wherein the second cell is dischargeable at a relatively high electrical current of about 1 to about 4 amperes such that should a background voltage of the second cell fall below a working voltage of the first cell, the second cell is recharged by the first cell to equalize each of their working voltages.

25. The electrochemical battery of claim 24 wherein the first cell is of a $Li/CF_x$ couple.

26. The electrochemical battery of claim 24 wherein the second cell is of a Li/SVO couple.

27. The electrochemical battery of claim 24 powering a cardiac defibrillator.

28. A method for providing an electrochemical battery capable of discharge at both a substantially constant discharge rate and under a current pulse discharge application, which comprises:
a) providing a casing;
b) housing a first electrochemical cell inside the casing by the steps of:

i) providing a first anode comprising an alkali metal and electrically associating the alkali metal with a first anode current collector connected to a first anode terminal; and ii) providing a first cathode of a first cathode active material and electrically associating the first cathode active material with a first cathode current collector connected to a first cathode terminal; and c) housing a second electrochemical cell inside the casing by the step of:

i) providing a second anode comprising the alkali metal and electrically associating the alkali metal with a second anode current collector connected to a second anode terminal;

ii) providing a second cathode of a second cathode active material and electrically associating the second cathode active material with a second cathode current collector connected to a second cathode terminal; and iii) activating the first and second electrochemical cells with a nonaqueous electrolyte, wherein the casing does not have a wall separating the first cell from the second cell so that the activating electrolyte is common to both cells;

d) connecting the first and second anode terminals to a common anode lead connectable to a load and connecting the first and second cathode terminals to a common cathode lead connectable to the load; and e) wherein the first cathode active material has a relatively high energy density but a relatively low rate capability and the second cathode active material has a relatively low energy density but a relatively high rate capability.

29. The method of claim 28 including providing the first and the second electrochemical cells dischargeable under a substantially constant discharge rate and under a current pulse discharge application.

30. The method of claim 28 including electrically connecting the first and second anode current collectors to the casing as the common anode lead.

31. The method of claim 25 including electrically insulating the first and second cathode terminals from the casing.

32. The method of claim 25 including electrically insulating the first and second anode terminals from the casing.

33. The method of claim 28 including providing the anode comprised of lithium.

34. The method of claim 28 including providing the nonaqueous electrolyte comprising a first solvent selected from the group consisting of an ester, an ether, a dialkyl carbonate, and mixtures thereof, and a second solvent selected from the group consisting of a cyclic carbonate, a cyclic ester, a cyclic amide, and mixtures thereof.

35. The method of claim 25 including selecting the first cathode active material from the group consisting of $CF_x$, $Ag_2O$, $Ag_2O_2$, $CuF$, $Ag_2CrO_4$, $MnO_2$, silver vanadium oxide, and mixtures thereof.

36. The method of claim 25 including selecting the second cathode active material from the group consisting of silver vanadium oxide, copper silver vanadium oxide, $V_2O_5$, $MnO_2$, $LiCoO_2$, $LiNiO_2$, $LiMnO_2$, $CuO_2$, TiS, $Cu_2S$, FeS, $FeS_2$, copper oxide, copper vanadium oxide, and mixtures thereof.

* * * * *